United States Patent
O'Leary

(10) Patent No.: US 6,701,917 B2
(45) Date of Patent: Mar. 9, 2004

(54) DOSE COUNTER FOR MEDICAMENT INHALER

(75) Inventor: David O'Leary, Essex (GB)

(73) Assignee: Norton Healthcare, Ltd., London (GB)

( * ) Notice: Subject to any disclaimer, the term of this patent is extended or adjusted under 35 U.S.C. 154(b) by 0 days.

(21) Appl. No.: 09/888,198

(22) Filed: Jun. 23, 2001

(65) Prior Publication Data

US 2002/0073996 A1 Jun. 20, 2002

Related U.S. Application Data

(60) Provisional application No. 60/213,668, filed on Jun. 23, 2000, and provisional application No. 60/213,382, filed on Jun. 23, 2000.

(51) Int. Cl.$^7$ .............................................. A61M 11/00
(52) U.S. Cl. .............................. 128/200.23; 128/200.14
(58) Field of Search ....................... 128/200.11, 200.12, 128/200.14, 200.18, 200.24, 200.23, 203.15, 203.19, 203.23, 205.23; 116/307, 308, 311–315, 318, 319; 222/38, 36, 162

(56) References Cited

U.S. PATENT DOCUMENTS

| | | | | |
|---|---|---|---|---|
| 5,020,527 A | * | 6/1991 | Dessertine ............. | 128/200.23 |
| 5,437,270 A | | 8/1995 | Braithwaite | |
| 5,544,647 A | * | 8/1996 | Jewett et al. .......... | 128/200.23 |
| 5,549,101 A | | 8/1996 | Trofast et al. | |
| 5,657,748 A | | 8/1997 | Braithwaite ............ | 128/203.15 |
| 5,740,792 A | * | 4/1998 | Ashley et al. .......... | 128/203.15 |
| 5,833,066 A | * | 11/1998 | Hargus et al. ............... | 206/438 |
| 5,840,279 A | | 11/1998 | Narodylo et al. .............. | 424/46 |
| 5,988,496 A | * | 11/1999 | Bruna ....................... | 235/91 R |
| 6,029,659 A | * | 2/2000 | O'Connor .............. | 128/203.12 |
| 6,142,145 A | * | 11/2000 | Dagsland et al. ....... | 128/203.15 |
| 6,142,339 A | * | 11/2000 | Blacker et al. ................ | 222/23 |
| 6,240,918 B1 | * | 6/2001 | Ambrosio et al. ...... | 128/203.15 |
| 6,283,365 B1 | * | 9/2001 | Bason ......................... | 235/116 |
| 6,328,037 B1 | * | 12/2001 | Scarrott et al. .......... | 128/205.23 |
| 6,336,453 B1 | * | 1/2002 | Scarrott et al. .......... | 128/200.23 |
| 6,360,739 B1 | * | 3/2002 | Rand et al. ............. | 128/200.23 |
| 6,431,168 B1 | * | 8/2002 | Rand et al. ............. | 128/200.23 |
| 6,446,627 B1 | * | 9/2002 | Bowman et al. ........ | 128/200.23 |

FOREIGN PATENT DOCUMENTS

| | | | | |
|---|---|---|---|---|
| GB | 2 320 489 A | * | 6/1998 | .......... A61M/15/00 |
| WO | WO 92/17231 | * | 10/1992 | .......... A61M/11/00 |
| WO | WO94/053589 A1 | | 3/1994 | |
| WO | WO 97/30743 | | 8/1997 | |
| WO | WO 00/01612 | * | 1/2000 | |

* cited by examiner

Primary Examiner—Henry Bennett
Assistant Examiner—Nihir Patel
(74) Attorney, Agent, or Firm—McDermott, Will & Emery

(57) ABSTRACT

A new and improved inhaler includes an accurate and consistent mechanical dose metering system that dispenses dry powdered medicament in discrete amounts or doses for patient inhalation, a pressure relief system that manages pressure within a medicament reservoir of the inhaler to ensure consistently dispensed doses, and a dose counting system indicating the number of doses remaining in the inhaler.

14 Claims, 8 Drawing Sheets

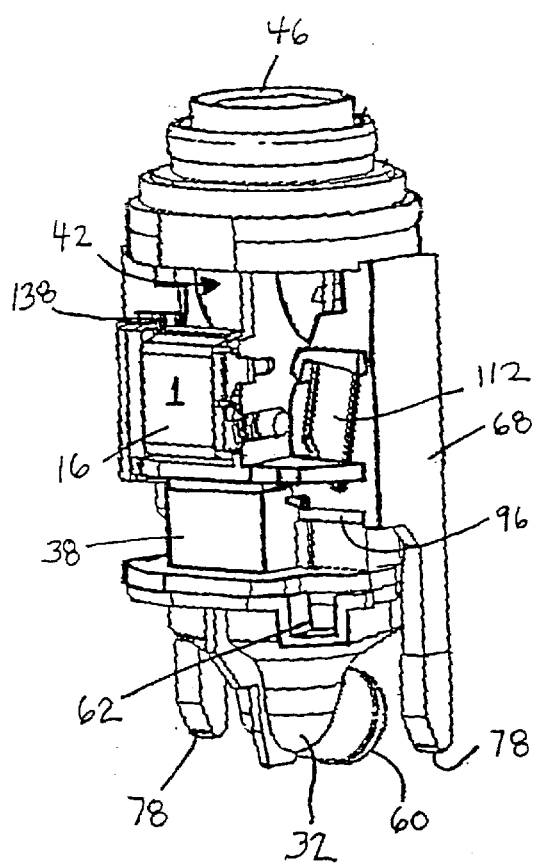
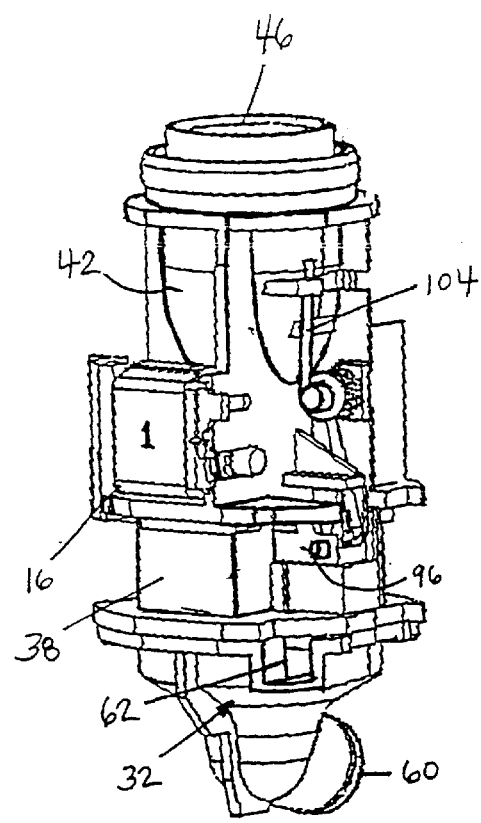
FIG. 3
FIG. 4

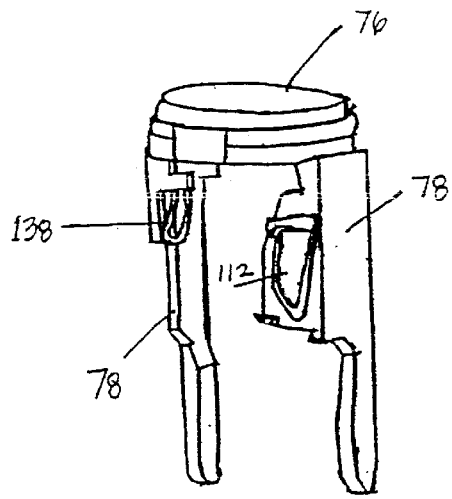
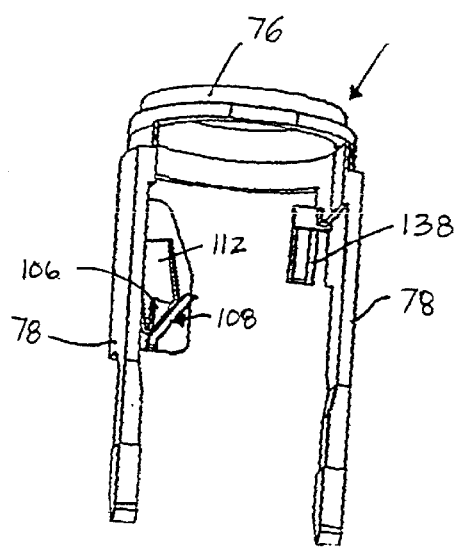
FIG. 11
FIG. 12
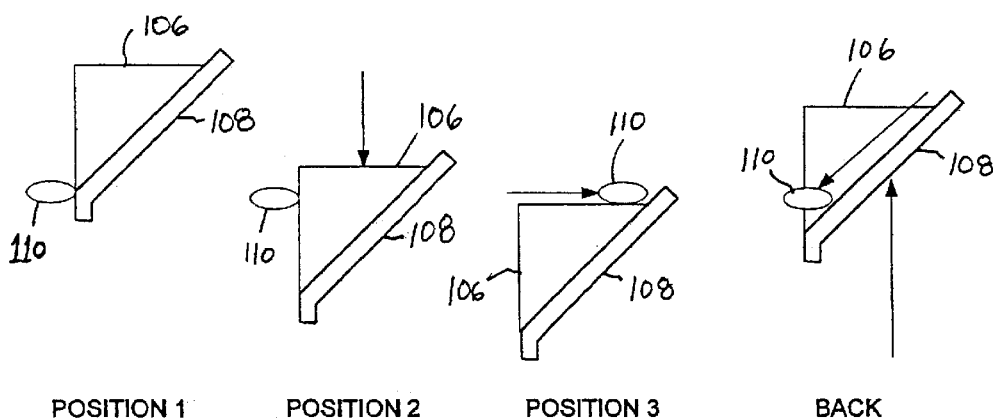
POSITION 1   POSITION 2   POSITION 3   BACK
FIG. 13

DOSE COUNTER FOR MEDICAMENT INHALER

CROSS-REFERENCE TO RELATED APPLICATIONS

The present application claims priority to co-pending provisional U.S. patent application Ser. No. 60/213,668, filed Jun. 23, 2000 (entitled "Breath-Actuated Dry Powder Inhaler"), and co-pending provisional U.S. patent application Ser. No. 60/213,382, filed Jun. 23, 2000 (entitled "De-Agglomerator for Breath-Actuated Dry Powder Inhaler"). Each of these co-pending applications is assigned to the assignee of the present disclosure and incorporated herein by reference.

FIELD OF THE DISCLOSURE

The present disclosure relates to an apparatus and method for administering medicament for inhalation by a patient and, more particularly, to a dry powdered medicament inhaler.

BACKGROUND OF THE DISCLOSURE

Metered dose medicament inhalers are well known for dispensing medicament to the lungs of a patient, for treating asthma for example. Existing types of medicament dispensing inhalers include pressurized propellant inhalers, aqueous solution inhalers, and dry-powdered inhalers.

U.S. Pat. No. 5,503,144 to Bacon, for example, shows a dry powdered inhaler. The inhaler includes a reservoir for containing a dry powdered medicament, a metering chamber for removal of the powdered medicament from the reservoir in discrete amounts, and an air inlet for entraining the removed powdered medicament through a mouthpiece upon patient inhalation.

Another example is U.S. Pat. No. 5,971,951 to Ruskewicz, which shows an inhaler including a motor driven cam mechanism for extruding aqueous medicament through a porous membrane to form a medicament aerosol for inhalation by a patient. The inhaler also includes sensors, circuitry and a microprocessor that determines the rate of patient inhalation and operates the extrusion mechanism only upon adequate inhalation levels.

A pressurized propellant, or "aerosol" inhaler is shown in U.S. Pat. No. 5,447,150 to Bacon, which also discloses a simple, mechanical actuation assembly for ensuring that medicament is dispensed from the inhaler only upon adequate inhalation by a patient. The actuation assembly works by applying a pre-load to a valve of the aerosol container sufficient to cause a dose release, but prevents the release by applying a pneumatic resisting force. The dose of medicament is then released upon a patient inhalation strong enough to move a door within the assembly, which in turn releases the pneumatic resisting force.

What is still desired, however, is a new and improved inhaler for administering medicament for patient inhalation. Preferably, the new and improved inhaler can be used with dry powdered medicament. In addition, the new and improved inhaler will preferably include mechanical assemblies for metering doses of medicament, managing medicament reservoir pressure, and counting the number of doses remaining in the inhaler.

SUMMARY OF THE DISCLOSURE

The present disclosure, therefore, provides a new and improved medicament inhaler having a unique dose metering system. The inhaler includes a mouthpiece for patient inhalation, a delivery passageway for directing an inhalation induced air flow through the mouthpiece, a channel extending from the delivery passageway, and a reservoir for containing medicament, with the reservoir having a dispenser port connected to the channel. In a preferred form, the dose metering system includes a cup received in the channel, which is movable between the dispenser port and the delivery passageway, a cup spring biasing the cup towards one of the dispenser port and the passageway, and a yoke movable between at least two positions. The yoke includes a ratchet engaging the cup and preventing movement of the cup when the yoke is in one of the positions, and allowing movement of the cup when the yoke is in another of the positions.

The present disclosure also provides a medicament inhaler having a unique reservoir pressure system. The inhaler includes a sealed reservoir having a dispenser port, and a channel communicating with the dispenser port, and a cup assembly movably received in the channel. In a preferred form, the pressure system includes a pressure relief port in the channel, and a conduit providing fluid communication between an interior of the sealed reservoir and the pressure relief port of the channel. The cup assembly includes a recess adapted to receive medicament when aligned with the dispenser port, a first sealing surface adapted to seal the dispenser port when the recess is unaligned with the dispenser port, and a second sealing surface adapted to seal the pressure relief port when the recess is aligned with the dispenser port and unseal the pressure relief port when the recess is unaligned with the dispenser port.

The present disclosure additionally provides a medicament inhaler having a unique dose counter. The inhaler includes a mouthpiece for patient inhalation, a dose metering system including a pawl movable along a predetermined path during the metering of a dose of medicament to the mouthpiece by the dose metering system, and a dose counter. In a preferred form, the dose counter includes a bobbin, a rotatable spool, and a rolled ribbon received on the bobbin, rotatable about an axis of the bobbin. The ribbon has indicia thereon successively extending between a first end of the ribbon secured to the spool and a second end of the ribbon positioned on the bobbin. The dose counter also includes teeth extending radially outwardly from the spool into the predetermined path of the pawl so that the spool is rotated by the pawl and the ribbon advanced onto the spool during the metering of a dose to the mouthpiece.

Thus, the present disclosure provides a new and improved inhaler including a simple, accurate and consistent mechanical dose metering system that dispenses dry powdered medicament in discrete amounts or doses for patient inhalation, a reservoir pressure system that ensures consistently dispensed doses, and a dose counter indicating the number of doses remaining in the inhaler.

Further features and advantages of the presently disclosed inhaler will become more readily apparent to those having ordinary skill in the art to which the present disclosure relates from the drawings and the detailed description.

BRIEF DESCRIPTION OF THE DRAWINGS

So that those having ordinary skill in the art will more readily understand how to construct a dry powdered medicament inhaler in accordance with the present disclosure, a preferred embodiment is described below with reference to the drawing figures wherein:

FIG. 3 is a second side isometric view of a main assembly of the inhaler of FIG. 1;

FIG. 4 is a second side isometric view of the main assembly of the inhaler of FIG. 1, shown with a yoke removed;

FIG. 11 is a second side isometric view of the yoke of the inhaler of FIG. 1;

FIG. 12 is a first side isometric view of the yoke of the inhaler of FIG. 1, showing a ratchet and a push bar of the yoke;

FIG. 13 is a schematic illustration of lateral movement of a boss of the medicament cup in response to longitudinal movement of the ratchet and the push bar of the yoke of the inhaler of FIG. 1;

Like reference characters designate identical or corresponding components and units throughout the several views.

DETAILED DESCRIPTION OF THE PREFERRED EMBODIMENTS

Referring to FIGS. 1 through 16, the present disclosure provides a new and improved inhaler 10 for dispensing a dry-powdered medicament in metered doses for patient inhalation. The inhaler 10 of the present disclosure provides many beneficial features including but not limited to a dose metering system that dispenses dry powdered medicament in discrete amounts or doses for patient inhalation, a medicament reservoir pressure system for managing pressure within the reservoir, and a dose counting system indicating the number of doses remaining in the inhaler 10.

Figure 1:
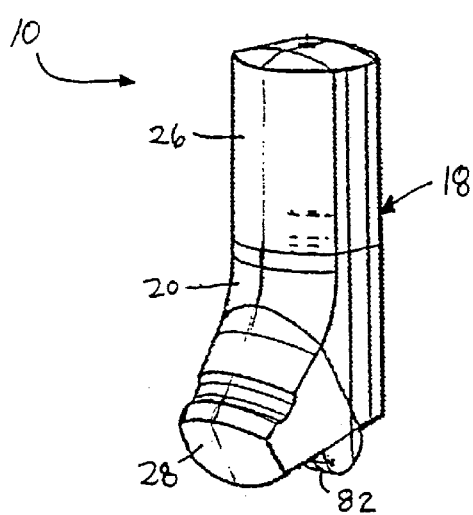
FIG. 1 is a first side isometric view of a dry powdered medicament inhaler according to the present disclosure.
Figure 2:
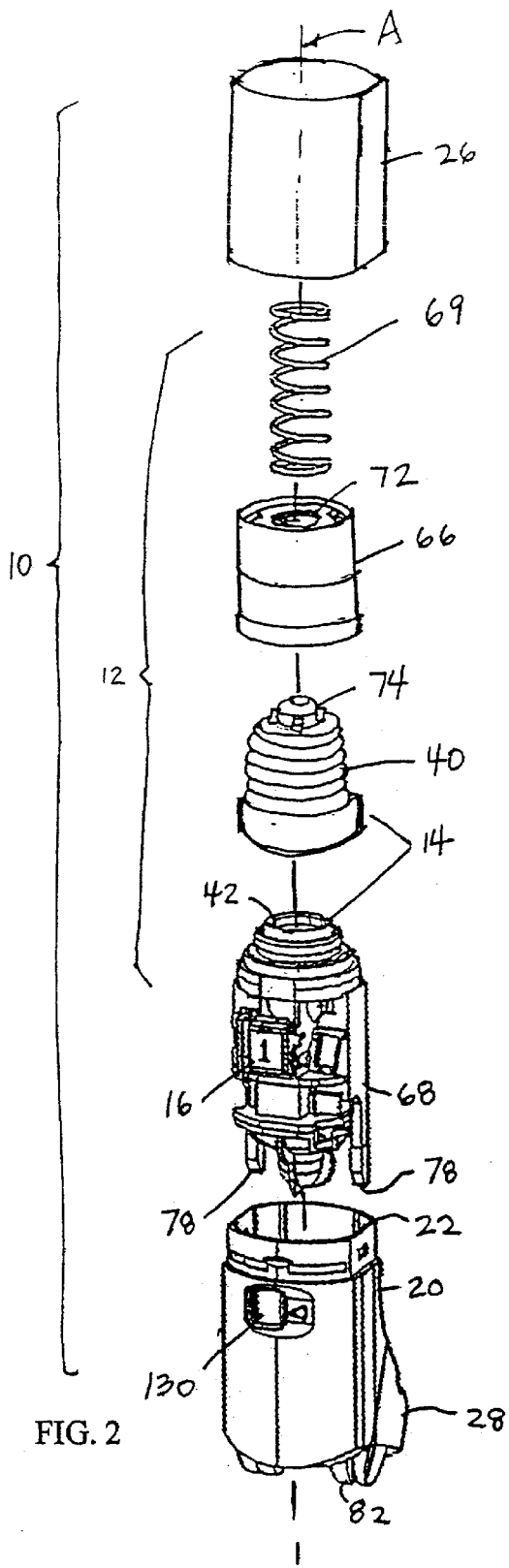
FIG. 2 is an exploded, second side isometric view of the inhaler of FIG. 1.

The inhaler 10 generally includes a housing 18, and an assembly 12 received in the housing (see FIG. 2). The housing 18 includes a case 20 having an open end 22 and a mouthpiece 24 for patient inhalation, a cap 26 secured to and closing the open end 22 of the case 20, and a cover 28 pivotally mounted to the case 20 for covering the mouthpiece 24 (see FIGS. 1, 2 and 9). The housing 18 is preferably manufactured from a plastic such as polypropylene, acetal or moulded polystyrene, but may be manufactured from metal or another suitable material.

The internal assembly 12 includes a reservoir 14 for containing dry powered medicament in bulk form, a de-agglomerator 32 that breaks down the medicament between a delivery passageway 34 and the mouthpiece 24, and a spacer 38 connecting the reservoir to the de-agglomerator.

Reservoir

The reservoir 14 is generally made up of a collapsible bellows 40 and a hopper 42 having an dispenser port 44 (see FIGS. 2–5 and 7–8) for dispensing medicament upon the bellows 40 being at least partially collapsed to reduce the internal volume of the reservoir. The hopper 42 is for holding the dry powder medicament in bulk form and has an open end 46 closed by the flexible accordion-like bellows 40 in a substantially air-tight manner. An air filter 48 covers the open end 46 of the hopper 42 and prevents dry powder medicament from leaking from the hopper 42 (see FIG. 7).

Spacer

A base 50 of the hopper 42 is secured to a spacer 38, which is in turn secured to the de-agglomerator 32 (see FIGS. 3–5 and 7–8). The hopper 42, the spacer 38, and the de-agglomerator 32 are preferably manufactured from a plastic such as polypropylene, acetal or moulded polystyrene, but may be manufactured from metal or another suitable material. The hopper 42, the spacer 38 and the de-agglomerator 32 are connected in a manner that provides an air tight seal between the parts. For this purpose heat or cold sealing, laser welding or ultrasonic welding could be used, for example.

The spacer 38 and the hopper 42 together define the medicament delivery passageway 34, which preferably includes a venturi 36 (see FIG. 16) for creating an entraining air flow. The spacer 38 defines a slide channel 52 communicating with the dispenser port 44 of the hopper 42, and a chimney 54 providing fluid communication between the medicament delivery passageway 34 and a supply port 56 of the de-agglomerator 32 (see FIGS. 7 and 8). The slide channel 52 extends generally normal with respect to the axis "A" of the inhaler 10.

De-Agglomerator

As its name implies, the de-agglomerator 32 breaks down agglomerates of dry powder medicament before the dry powder leaves the inhaler 10 through the mouthpiece 24. The de-agglomerator includes a swirl chamber 58 extending from the supply port 56 to an outlet port 60 connected to the mouthpiece 24 (see FIG. 16). The de-agglomerator 32 also includes two diametrically opposed inlet ports 62 that extend substantially tangential to the circular cross-section of the swirl chamber. Radial vanes 64 are positioned at the top of the swirl chamber and are sized such that at least a portion of breath-actuated air streams entering through the diametrically opposed inlet ports 62 collide with the vanes.

The inhaler 10 preferably includes a de-agglomerator of the type disclosed in co-pending provisional U.S. patent application Ser. No. 60/213,382, filed Jun. 23, 2000 (entitled "De-Agglomerator for Breath-Actuated Dry Powder Inhaler 10"), which has been incorporated herein by reference. It should be understood that although the inhaler 10 of the present disclosure is shown with a particular de-agglomerator 32, the inhaler 10 is not limited to use with the de-agglomerator shown and can be used with other types of de-agglomerators or a simple swirl chamber.

Dose Metering System

The dose metering system includes a first yoke 66 and a second yoke 68 mounted on the internal assembly 12 within the housing 18, and movable in a linear direction parallel with an axis "A" of the inhaler 10 (see FIG. 2). An actuation spring 69 is positioned between the cap 26 of the housing 18 and the first yoke 66 for biasing the yokes in a first direction towards the mouthpiece 24. In particular, the actuation spring 69 biases the first yoke 66 against the bellows 40 and the second yoke 68 against cams 70 mounted on the mouthpiece cover 28 (see FIG. 9).

The first yoke 66 includes an opening 72 that receives and retains a crown 74 of the bellows 40 such that the first yoke 66 pulls and expands the bellows 40 when moved towards the cap 26, i.e., against the actuation spring 69 (see FIG. 2). The second yoke 68 includes a belt 76, which receives the first yoke 66, and two cam followers 78 extending from the belt in a direction opposite the first yoke 66 (see FIGS. 3, 11 and 12), towards the cams 70 of the mouthpiece cover 28.

The dose metering system also includes the two cams 70 mounted on the mouthpiece cover 28 (see FIGS. 9 and 10), and movable with the cover 28 between open and closed positions. The cams 70 each include an opening 80 for allowing outwardly extending hinges 82 of the case 20 to pass therethrough and be received in first recesses 84 of the cover 28. The cams 70 also include bosses 86 extending outwardly and received in second recesses 88 of the cover 28, such that the cover 28 pivots about the hinges 82 and the cams 70 move with the cover 28 about the hinges.

Each cam 70 also includes first, second and third cam surfaces 90, 92, 94, and the cam followers 78 of the second yoke 68 are biased against the cam surfaces by the actuation spring 69. The cam surfaces 90, 92, 94 are arranged such the cam followers 78 successively engage the first cam surfaces 90 when the cover 28 is closed, the second cam surfaces 92 when the cover 28 is partially opened, and the third cam surfaces 94 when the cover 28 is fully opened. The first cam surfaces 90 are spaced further from the hinges 82 than the second and the third cam surfaces, while the second cam surfaces 92 are spaced further from the hinges 82 than the third cam surfaces 94. The cams 70, therefore, allow the yokes 66, 68 to be moved by the actuation spring 69 parallel with the axis "A" of the inhaler 10 in the first direction (towards the mouthpiece 24) through first, second and third positions as the cover 28 is opened. The cams 70 also push the yokes 66, 68 in a second direction parallel with the axis "A" (against the actuation spring 69 and towards the cap 26 of the housing 18) through the third, the second and the first positions as the cover 28 is closed.

The dose metering system further includes a cup assembly 96 movable between the dispenser port 44 of the reservoir 14 and the delivery passageway 34. The cup assembly 96 includes a medicament cup 98 mounted in a sled 100 slidably received in the slide channel 52 of the spacer 38 below the hopper 42 (see FIGS. 5 and 6). The medicament cup 98 includes a recess 102 adapted to receive medicament from the dispenser port 44 of the reservoir 14 and sized to hold a predetermined dose of dry powdered medicament when filled. The cup sled 100 is biased along the slide channel 52 from the dispenser port 44 of the hopper 42 towards the delivery passageway 34 by a cup spring 104, which is secured on the hopper 42 (see FIGS. 4 and 5).

Figure 5:
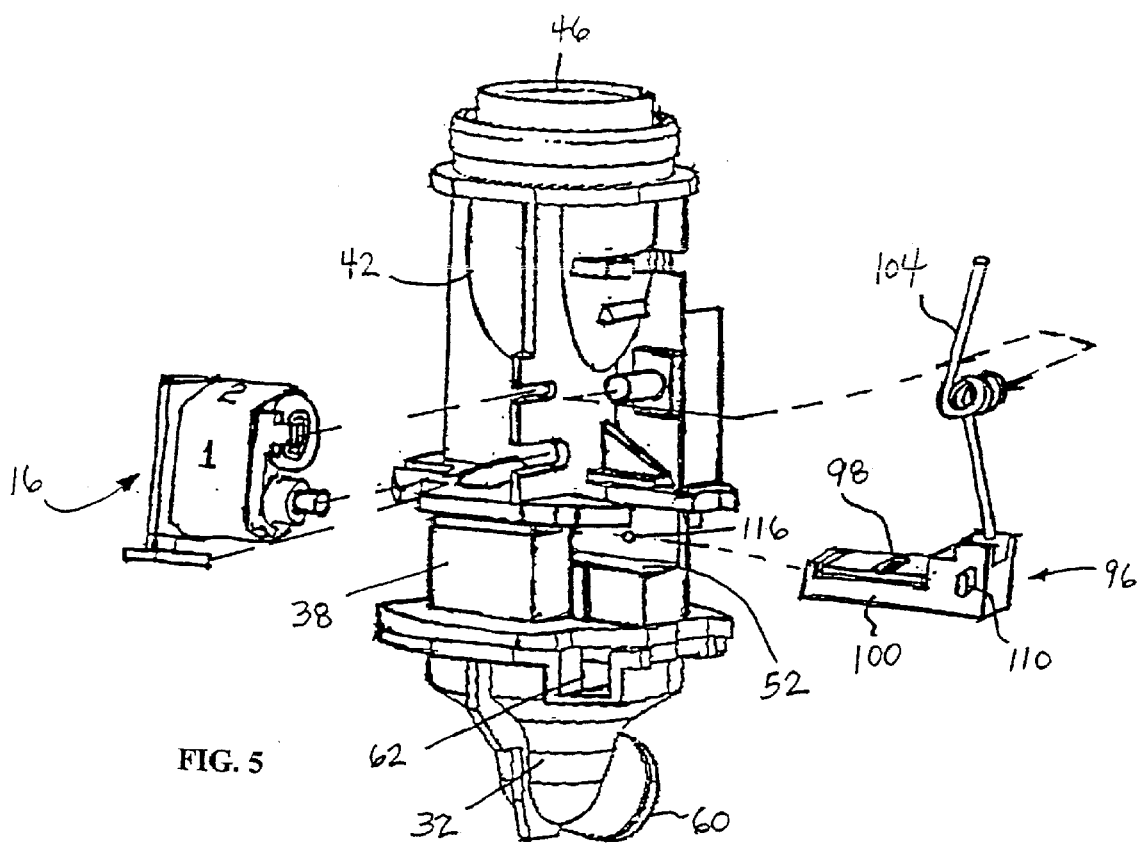
FIG. 5 is an exploded first side isometric view of the main assembly of the inhaler of FIG. 1.

The dose metering system also includes a ratchet 106 and a push bar 108 on one of the cam followers 78 of the second yoke 68 that engage a boss 110 of the cup sled 100 (see FIGS. 5, 11 and 12). The ratchet 106 is mounted on a flexible flap 112 and is shaped to allow the boss 110 of the sled 100 to depress and pass over the ratchet 106, when the boss 110 is engaged by the push bar 108. Operation of the dose metering system is discussed below.

Reservoir Pressure System

The reservoir pressure system includes a pressure relief conduit 114 in fluid communication with the interior of the reservoir 14 (see FIGS. 7 and 8), and a pressure relief port 116 in a wall of the slide channel 52 (see FIGS. 5 and 8) providing fluid communication with the pressure relief conduit 114 of the hopper 42.

Figure 6:
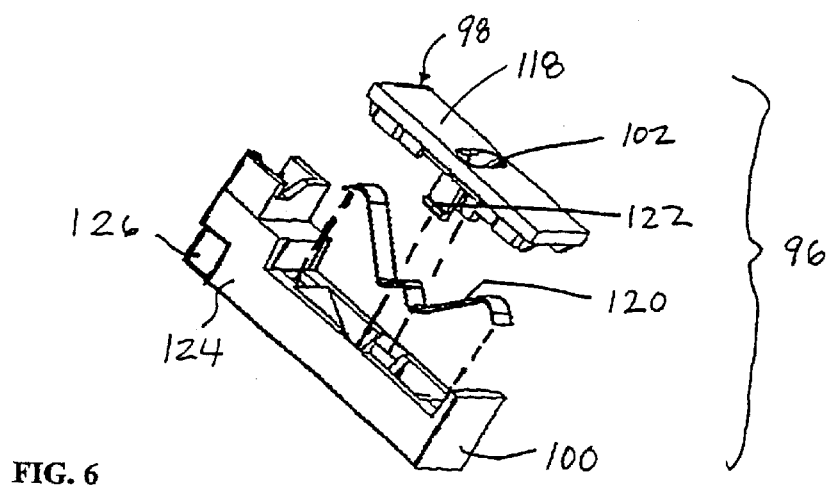
FIG. 6 is an exploded enlarged isometric view of a medicament cup of the inhaler of FIG. 1.
Figure 7:
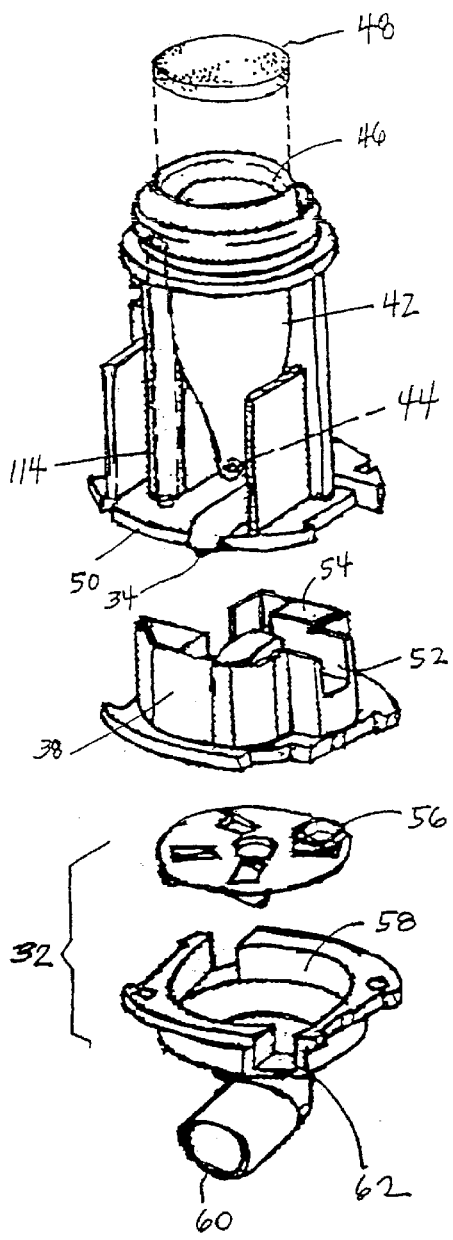
FIG. 7 is an exploded first side isometric view of a hopper and a de-agglomerator of the inhaler of FIG. 1.
Figure 8:
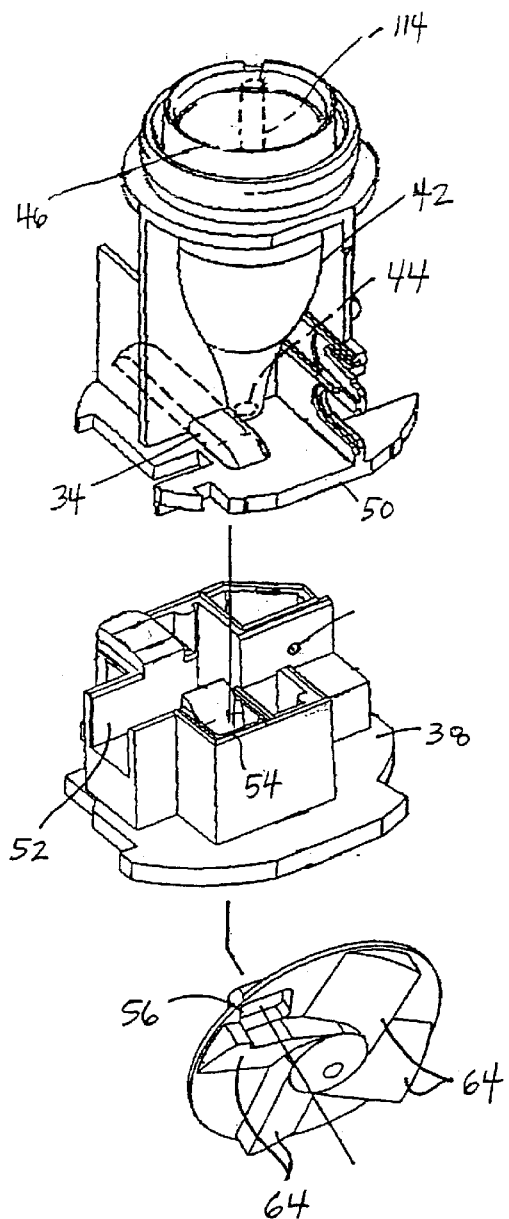
FIG. 8 is an exploded second side isometric view of the hopper and a swirl chamber roof of the de-agglomerator of the inhaler of FIG. 1.
Figure 9:
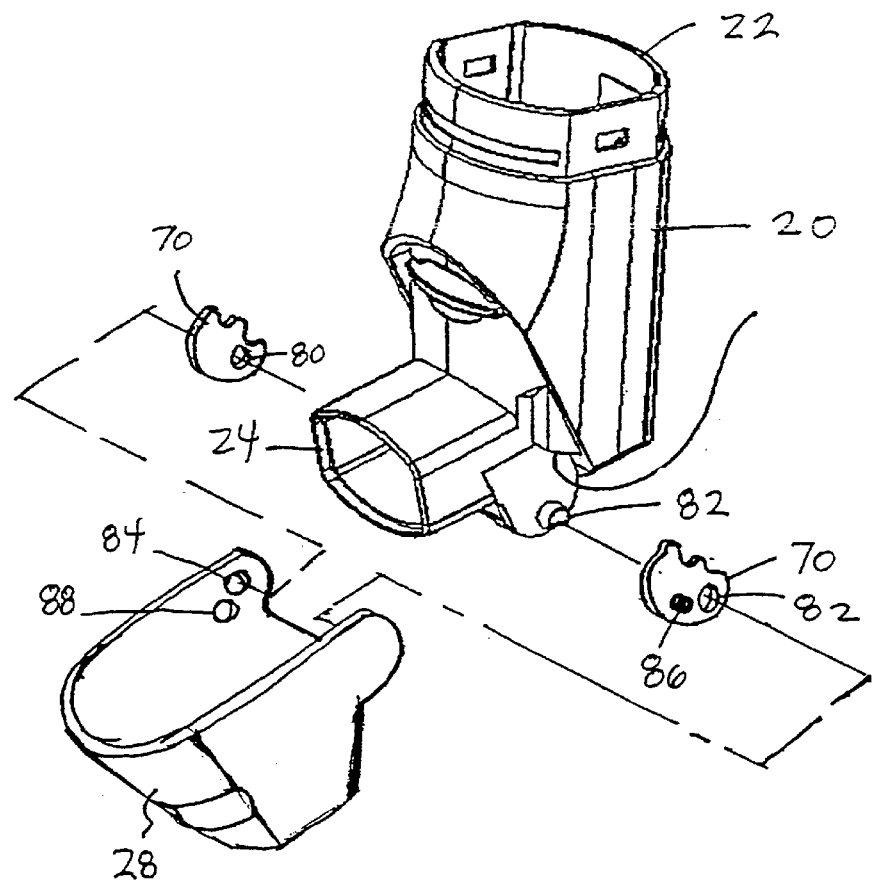
FIG. 9 is an exploded first side isometric view of a case, cams and a mouthpiece cover of the inhaler of FIG. 1.
Figure 10:
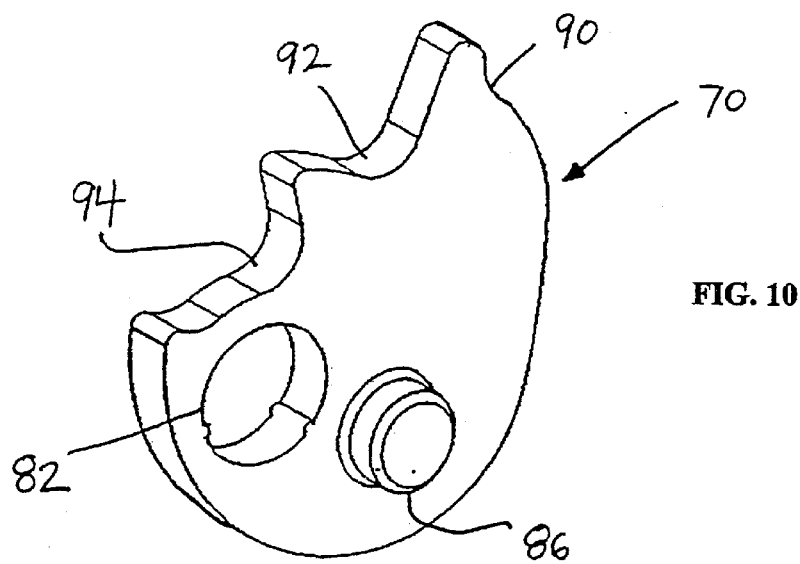
FIG. 10 is an enlarged side isometric view of one of the cams of the inhaler of FIG. 1.

The medicament cup assembly 96 includes a first sealing surface 118 adapted to seal the dispenser port 44 upon the cup assembly being moved to the delivery passageway 34 (see FIGS. 5 and 6). A sealing spring 120 is provided between the sled 100 and the cup 98 for biasing the medicament cup 98 against a bottom surface of the hopper 42 to seal the dispenser port 44 of the reservoir 14. The cup 98 includes clips 122 that allow the cup to be biased against the reservoir, yet retain the cup in the sled 100.

The sled 100 includes a second sealing surface 124 adapted to seal the pressure relief port 116 when the recess 102 of the cup 98 is aligned with the dispenser port 44, and an indentation 126 (see FIG. 6) adapted to unseal the pressure relief port 116 when the first sealing surface 118 is aligned with the dispenser port 44. Operation of the pressure system is discussed below.

Dose Counting System

The dose counting system 16 is mounted to the hopper 42 and includes a ribbon 128, having successive numbers or other suitable indicia printed thereon, in alignment with a transparent window 130 provided in the housing 18 (see FIG. 2). The dose counting system 16 includes a rotatable bobbin 132, an indexing spool 134 rotatable in a single direction, and the ribbon 128 rolled and received on the bobbin 132 and having a first end 127 secured to the spool 134, wherein the ribbon 128 unrolls from the bobbin 132 so that the indicia is successively displayed as the spool 134 is rotated or advanced.

The spool 134 is arranged to rotate upon movement of the yokes 66, 68 to effect delivery of a dose of medicament from the reservoir 14 into the delivery passageway 34, such that the number on the ribbon 128 is advanced to indicate that another dose has been dispensed by the inhaler 10. The ribbon 128 can be arranged such that the numbers, or other suitable indicia, increase or decrease upon rotation of the spool 134. For example, the ribbon 128 can be arranged such that the numbers, or other suitable indicia, decrease upon rotation of the spool 134 to indicate the number of doses remaining in the inhaler 10. Alternatively, the ribbon 128 can be arranged such that the numbers, or other suitable indicia, increase upon rotation of the spool 134 to indicate the number of doses dispensed by the inhaler 10.

The indexing spool 134 preferably includes radially extending teeth 136, which are engaged by a pawl 138 extending from one of the cam followers 78 (see FIGS. 3 and 11) of the second yoke 68 upon movement of the yoke to rotate, or advance, the indexing spool 134. More particularly, the pawl 138 is shaped and arranged such that it engages the teeth 136 and advances the indexing spool 134 only upon the mouthpiece 24 cover 28 being closed and the yokes 66, 68 moved back towards the cap 26 of the housing 18.

Figure 14:
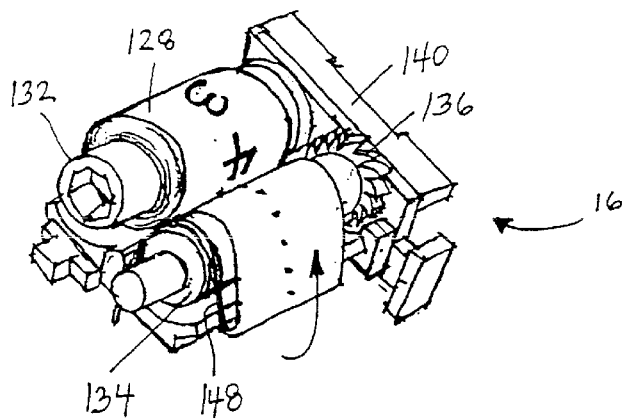
FIG. 14 is an enlarged isometric view of a dose counter of the inhaler of FIG. 1.
Figure 15:
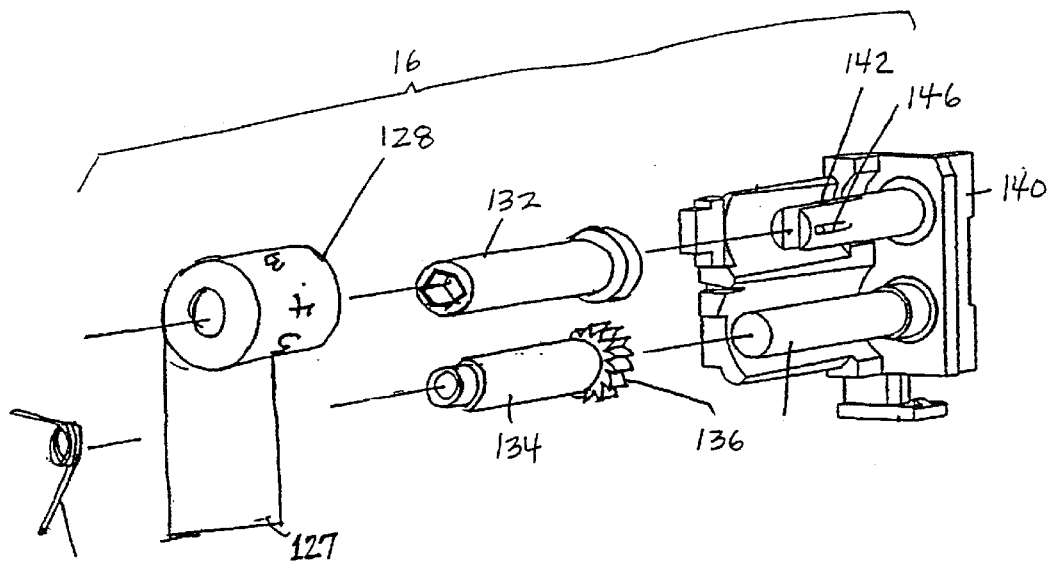
FIG. 15 is an exploded enlarged isometric view of the dose counter of the inhaler of FIG. 1.

The dose counting system 16 also includes a chassis 140 that secures the dose counting system to the hopper 42 and includes shafts 142, 144 for receiving the bobbin 132 and the indexing spool 134. The bobbin shaft 142 is preferably forked and includes radially nubs 146 for creating a resilient resistance to rotation of the bobbin 132 on the shaft 142. A clutch spring 148 is received on the end of the indexing spool 134 and locked to the chassis 140 to allow rotation of the spool 134 in only a single direction (counter-clockwise as shown in FIG. 14). Operation of the dose counting system 16 is discussed below.

Operation

FIG. 13 illustrates the relative movements of the boss 110 of the cup sled 100, and the ratchet 106 and the push bar 108 of the second yoke 68 as the mouthpiece cover 28 is opened and closed. In the first position of the yokes 66, 68 (wherein the cover 28 is closed and the cam followers 78 are in contact with the first cam surfaces 90 of the cams 70), the ratchet 106 prevents the cup spring 104 from moving the cup sled 100 to the delivery passageway 34. The dose metering system is arranged such that when the yokes are in the first position, the recess 102 of the medicament cup 98 is directly aligned with the dispenser port 44 of the reservoir 14 and the pressure relief port 116 of the spacer 38 is sealed by the second sealing surface 124 of the cup sled 100.

Upon the cover 28 being partially opened such that the second cam surfaces 92 of the cams 70 engage the cam followers 78, the actuator spring 69 is allowed to move the yokes 66, 68 linearly towards the mouthpiece 24 to the second position and partially collapse the bellows 40 of the medicament reservoir 14. The partially collapsed bellows 40 pressurizes the interior of the reservoir 14 and ensures medicament dispensed from the dispenser port 44 of the reservoir fills the recess 102 of the medicament cup 98 such that a predetermined dose is provided. In the second position, however, the ratchet 106 prevents the cup sled 100 from being moved to the delivery passageway 34, such that the recess 102 of the medicament cup 98 remains aligned with the dispenser port 44 of the reservoir 14 and the pressure relief port 116 of the spacer 38 remains sealed by the second sealing surface 124 of the cup assembly 96.

Upon the cover 28 being fully opened such that the third cam surfaces 94 engage the cam followers 78, the actuator spring 69 is allowed to move the yokes 66, 68 further towards the mouthpiece 24 to the third position. When moved to the third position, the ratchet 106 disengages, or falls below the boss 110 of the cup sled 100 and allows the cup sled 100 to be moved by the cup spring 104, such that the filled recess 102 of the cup 98 is position in the venturi 36 of the delivery passageway 34 and the dispenser port 44 of the reservoir 14 is sealed by the first sealing surface 118 of the cup assembly 96. In addition, the pressure relief port 116 is uncovered by the indentation 126 in the side surface of the sled 100 to release pressure from the reservoir 14 and allow the bellows 40 to further collapse and accommodate the movement of the yokes 66, 68 to the third position. The inhaler 10 is then ready for inhalation by a patient of the dose of medicament placed in the delivery passageway 34.

Figure 16:
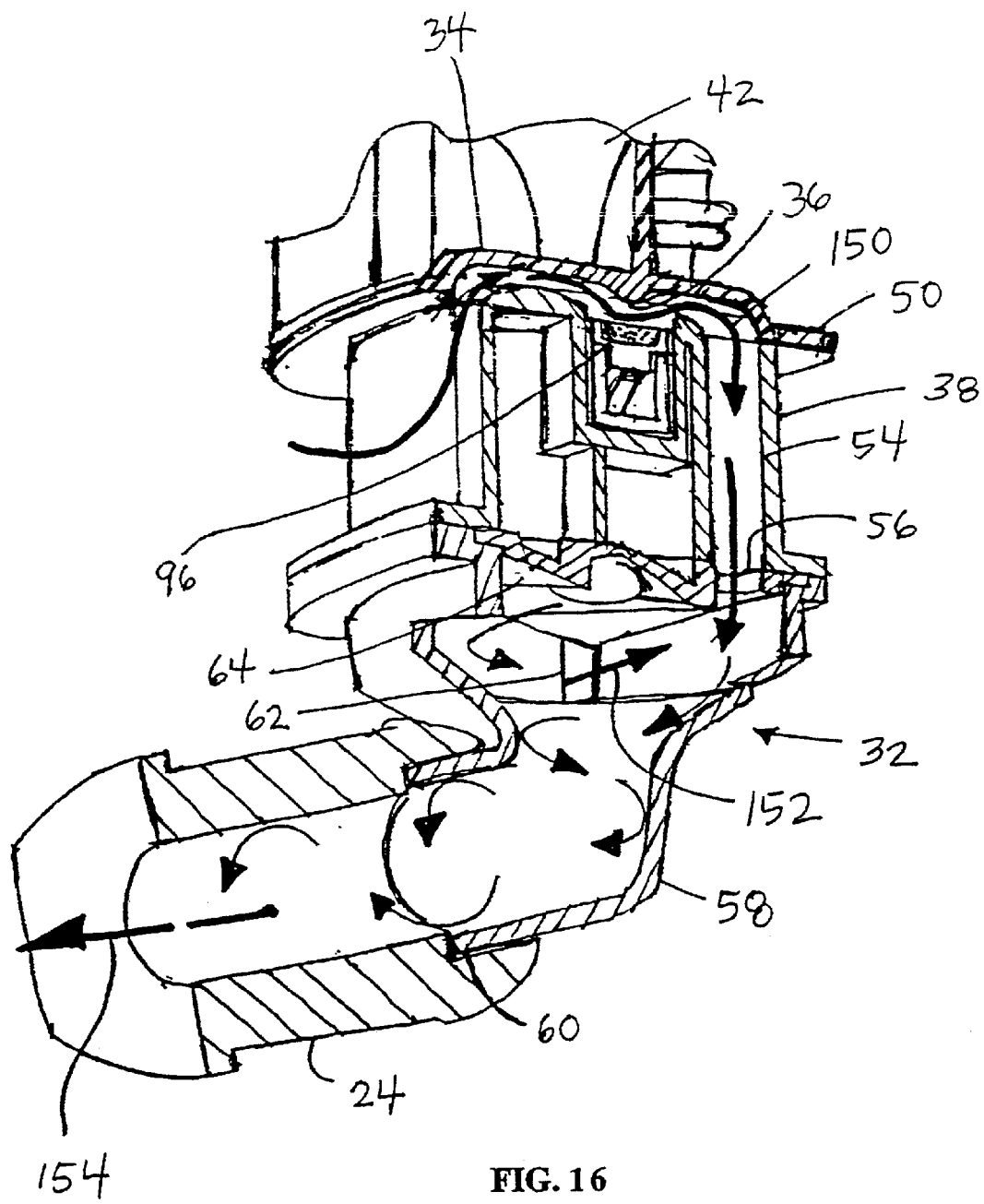
FIG. 16 is an enlarged isometric view, partially in section, of a portion of the inhaler of FIG. 1 illustrating medicament inhalation through the inhaler.

As shown in FIG. 16, a breath-induced air stream 150 diverted through the delivery passageway 34 passes through the venturi 36, entrains the medicament and carries the medicament into the de-agglomerator 32 of the inhaler 10. Two other breath-induced air streams 152 (only one shown) enter the de-agglomerator 32 through the diametrically opposed inlet ports 62 and combine with the medicament entrained air stream 150 from the delivery passageway 34. The combined flows 154 and entrained dry powder medicament then travel to the outlet port 60 of the de-agglomerator and pass through the mouthpiece 24 for patient inhalation.

Once inhalation is completed, the mouthpiece cover 28 can be closed. When the cover 28 is closed, the trigger cams 70 force the yokes 66, 68 upwardly such that the first yoke 66 expands the bellows 40, and the pawl 138 of the second yoke 68 advances the indexing spool 134 of the dose counting system 16 to provide a visual indication of a dose having been dispensed. In addition, the cup assembly 96 is forced back to the first position by the pusher bar 108 of the upwardly moving second yoke 68 (see FIG. 13) such that the boss 110 of the cup sled 100 is engaged and retained by the ratchet 106 of the second yoke 68.

It should be understood that the foregoing detailed description and preferred embodiment are only illustrative of inhalers constructed in accordance with the present disclosure. Various alternatives and modifications to the presently disclosed inhalers can be devised by those skilled in the art without departing from the spirit and scope of the present disclosure. For example, the medicament cup could be provided on a rotary sled, advanced by movement of the yokes. In addition, the outlet port of the pressure relief could be provided in other locations than the side wall of the slide channel. Furthermore, the dose counting system could be adapted to provide an audible indications in addition to a visual indication of a dispensed dose. Accordingly, the present disclosure is intended to embrace all such alternatives and modifications that fall within the spirit and scope of an inhaler as recited in the appended claims.

What is claimed is:

1. A medicament inhaler comprising:
   a mouthpiece for patient inhalation;
   a dose meter including a pawl movable along a predetermined path during the metering of a dose of medicament to the mouthpiece;
   a dose counter including,
      a bobbin,
      a rotatable spool,
      a rolled ribbon received on the bobbin and rotatable about an axis of the bobbin, the ribbon having indicia thereon successively extending between a first end of the ribbon secured to the spool and a second end of the ribbon positioned on the bobbin, and
      teeth extending radially outwardly from the spool into the predetermined path of the pawl so that the spool is rotated by the pawl and the ribbon is advanced onto the spool during the metering of a dose.

2. An inhaler according to claim 1, wherein the spool rotates in a single direction.

3. An inhaler according to claim 1, wherein the dose counter includes a clutch spring secured to the spool and allowing rotation of the spool in a single direction.

4. An inhaler according to claim 1, wherein the indicia comprises numbers.

5. An inhaler according to claim 1, wherein the indicia are provided on a radially outwardly facing surface of the rolled ribbon.

6. An inhaler according to claim 1, wherein the predetermined path of the pawl is linear.

7. An inhaler according to claim 1, wherein the pawl moves in first and second directions along the predetermined path and is adapted to engage the teeth and advance the spool upon movement in the second direction.

8. An inhaler according to claim 1, further comprising a housing containing the dose counter and include a transparent window over the indicia of the ribbon.

9. An inhaler according to claim 1, further comprising a medicament reservoir including a dispensing port, and the dose meter meters a dose of medicament from the dispensing port to the mouthpiece.

10. An inhaler according to claim 9, wherein the reservoir is adapted to contain dry powdered medicament in bulk form.

11. An inhaler according to claim 1, wherein the indicia comprises numbers arranged to successively decrease as the ribbon is advanced onto the spool.

12. A medicament inhaler comprising:
   A. a housing having a case, a mouthpiece for patient inhalation, and a cover pivotally mounted to the case for covering the mouthpiece, said cover being movable between an opened position and a closed position;
   B. a dose counter received in said housing, said dose counter comprising:
      a bobbin,
      a rotatable spool,
      a rolled ribbon received on the bobbin and rotatable about an axis of the bobbin, the ribbon having indicia thereon successively extending between a first end of the ribbon secured to the spool and a second end of the ribbon positioned on the bobbin,
      teeth extending radially outwardly from the spool; and
   C. transmission means engaging with said cover and said teeth, such that said spool is rotated by said transmission means when said cover moves from an opened position to a closed position or moves from a closed position to an opened position.

13. A medicament inhaler according to claim 12, wherein said transmission means comprises at least one cam pivotally connected to said case and said cover, at least one yoke received within said case, said at least one yoke having at least one cam follower adapted for engaging with said cam, and a pawl extending from said yoke for engaging with said teeth.

14. A medicament inhaler according to claim 12 further comprising reverse rotation prevention means to prevent reverse rotation of said spool.

* * * * *